US011337833B2

(12) United States Patent
Sawyer et al.

(10) Patent No.: US 11,337,833 B2
(45) Date of Patent: May 24, 2022

(54) MODULAR PROSTHETICS DEVICES

(71) Applicants: University of Florida Research Foundation, Inc., Gainesville, FL (US); Brian P. Bartlett, Seattle, WA (US)

(72) Inventors: Wallace Gregory Sawyer, Gainesville, FL (US); Brian P. Bartlett, Seattle, WA (US); Derek L. Hood, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 122 days.

(21) Appl. No.: 16/643,372

(22) PCT Filed: Aug. 31, 2018

(86) PCT No.: PCT/US2018/049085
§ 371 (c)(1),
(2) Date: Feb. 28, 2020

(87) PCT Pub. No.: WO2019/046715
PCT Pub. Date: Mar. 7, 2019

(65) Prior Publication Data
US 2021/0059842 A1 Mar. 4, 2021

Related U.S. Application Data

(60) Provisional application No. 62/553,586, filed on Sep. 1, 2017.

(51) Int. Cl.
*A61F 2/78* (2006.01)
*A61F 2/60* (2006.01)
(Continued)

(52) U.S. Cl.
CPC .......... *A61F 2/78* (2013.01); *A61F 2/54* (2013.01); *A61F 2/60* (2013.01); *A61F 2/76* (2013.01);
(Continued)

(58) Field of Classification Search
CPC ...... A61F 2/64; A61F 2/78; A61F 2/54; A61F 2/60; A61F 2/76; A61F 2002/5006;
(Continued)

(56) References Cited

U.S. PATENT DOCUMENTS 2,568,053 A 9/1951 Catranis
4,463,459 A 8/1984 Shorter et al.
(Continued)

FOREIGN PATENT DOCUMENTS

GB 2253791 A 9/1992

OTHER PUBLICATIONS

International Search Report and Written Opinion dated Aug. 18, 2018 in co-pending PCT Patent Application No. PCT/US2018/049085.
(Continued)

*Primary Examiner* — Bruce E Snow
(74) *Attorney, Agent, or Firm* — Thomas | Horstemeyer, LLP

(57) ABSTRACT

Various examples are provided for modular prosthetic devices and their use. In one example, a device includes a chassis assembly including a joint portion; and an interchangeable module that can be removably attached to the
(Continued)

chassis assembly. The interchangeable modules can be configured for use in a wide variety of applications. The interchangeable modules can be quickly exchanged for different activities.

20 Claims, 15 Drawing Sheets

(51) Int. Cl.
    *A61F 2/64*     (2006.01)
    *A61F 2/54*     (2006.01)
    *A61F 2/76*     (2006.01)
    *A61F 2/50*     (2006.01)

(52) U.S. Cl.
    CPC .............. *A61F 2002/5006* (2013.01); *A61F 2002/5033* (2013.01); *A61F 2002/5083* (2013.01); *A61F 2002/543* (2013.01); *A61F 2002/607* (2013.01); *A61F 2002/7875* (2013.01); *A61F 2002/7887* (2013.01)

(58) Field of Classification Search
    CPC ...... A61F 2002/5033; A61F 2002/5083; A61F 2002/543; A61F 2002/607; A61F 2002/7875; A61F 2002/7887

See application file for complete search history.

(56) References Cited

U.S. PATENT DOCUMENTS

| | | | |
|---|---|---|---|
| 4,564,365 | A | 1/1986 | Winer et al. |
| 7,044,983 | B1 | 5/2006 | Cheng |
| 7,785,373 | B2 * | 8/2010 | Frye, Jr. .................. A61F 2/64 |
| | | | 623/45 |
| 8,414,658 | B2 | 4/2013 | Johnson et al. |
| 2004/0186592 | A1 | 9/2004 | Townsend et al. |
| 2016/0331558 | A1 | 11/2016 | Kampas et al. |
| 2021/0059842 | A1 * | 3/2021 | Sawyer .................. A61F 2/54 |

OTHER PUBLICATIONS

Bhala; et al. "Golf club holder for upper-extremity amputee golfers," Archives of Physical Medicine and Rehabilitation, vol. 63, Issue 7, pp. 339-341, Jul. 1982. https://www.ncbi.nlm.nih.gov/pubmed/7092536.

Supplementary EP Search Report dated May 26, 2021 for EP 18850320.

* cited by examiner

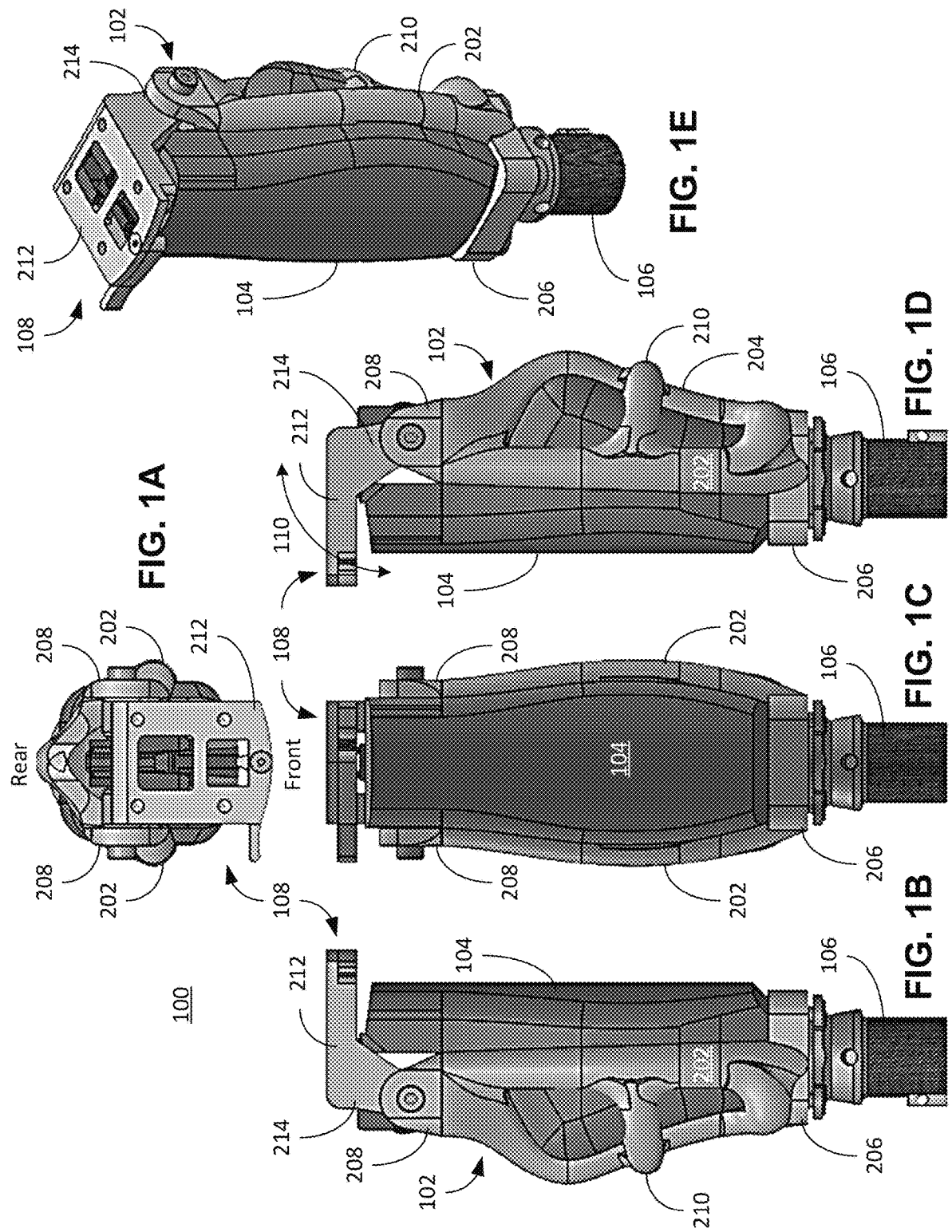

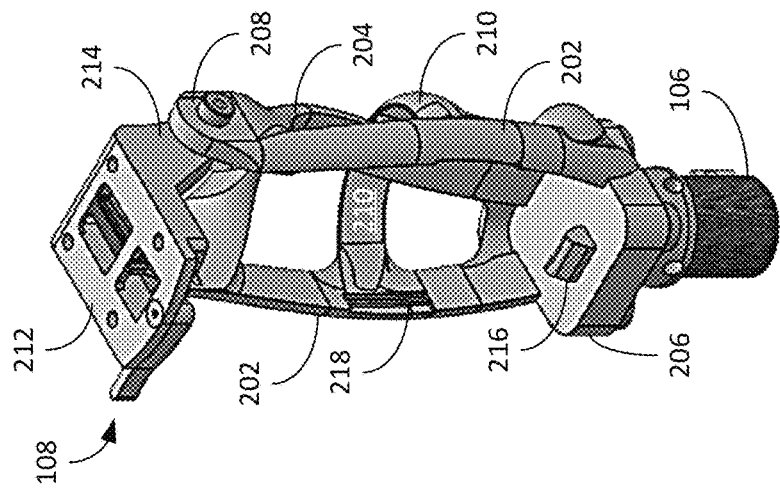
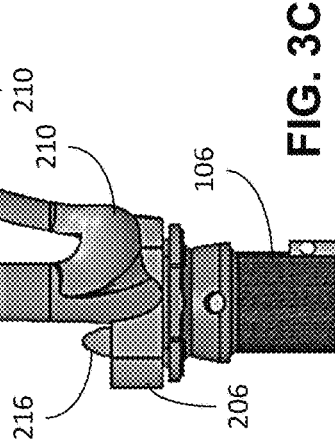
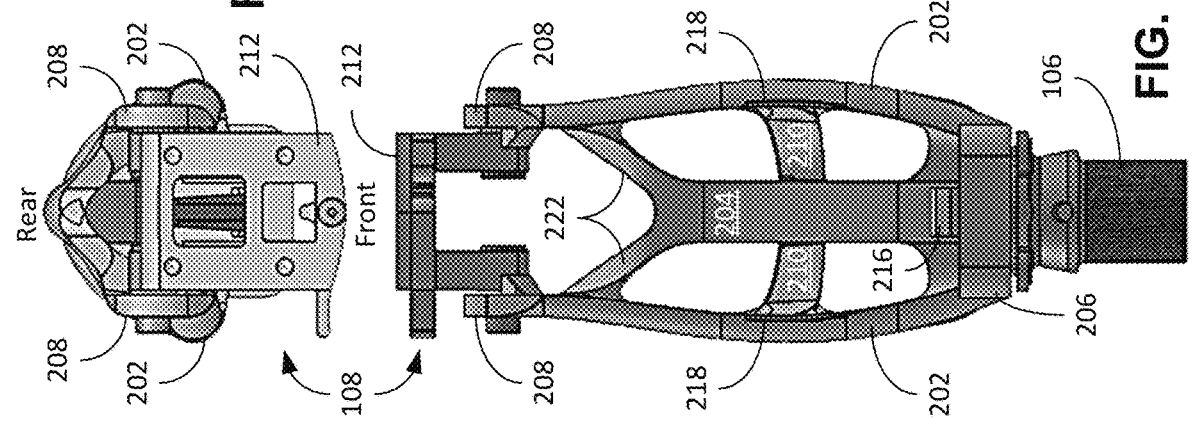

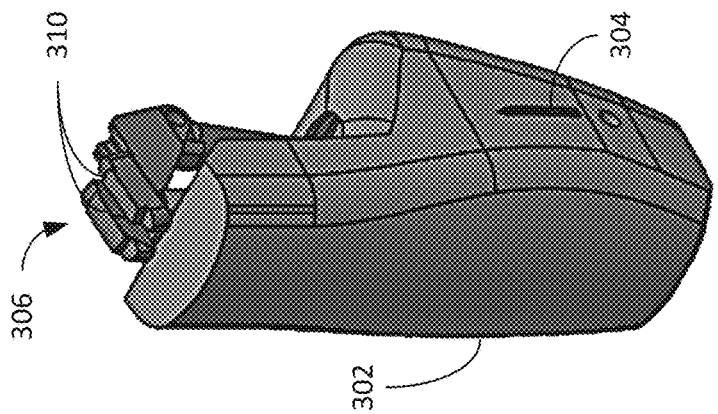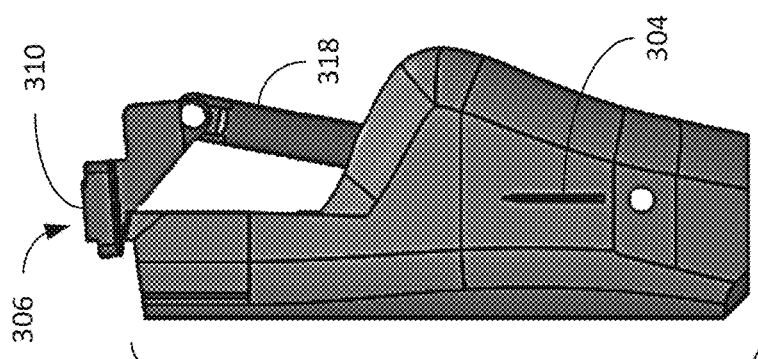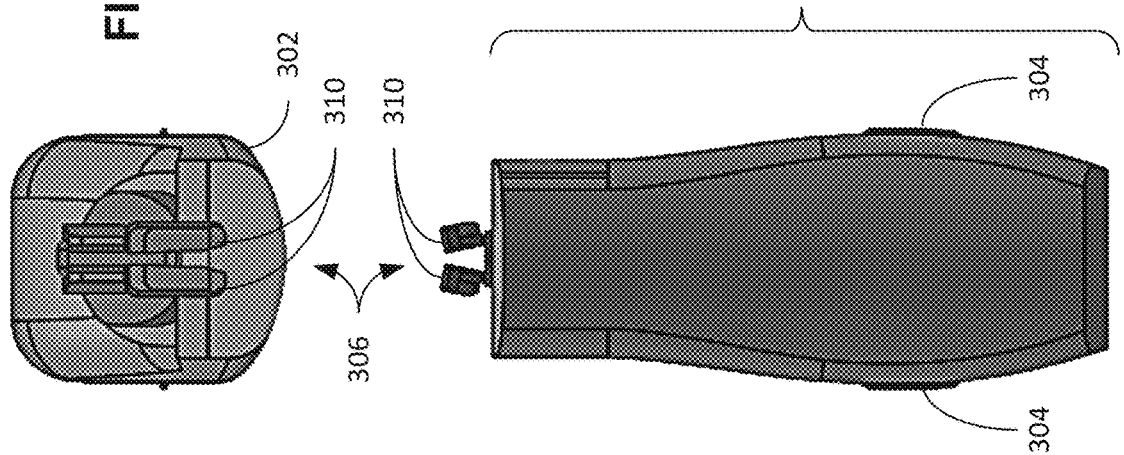

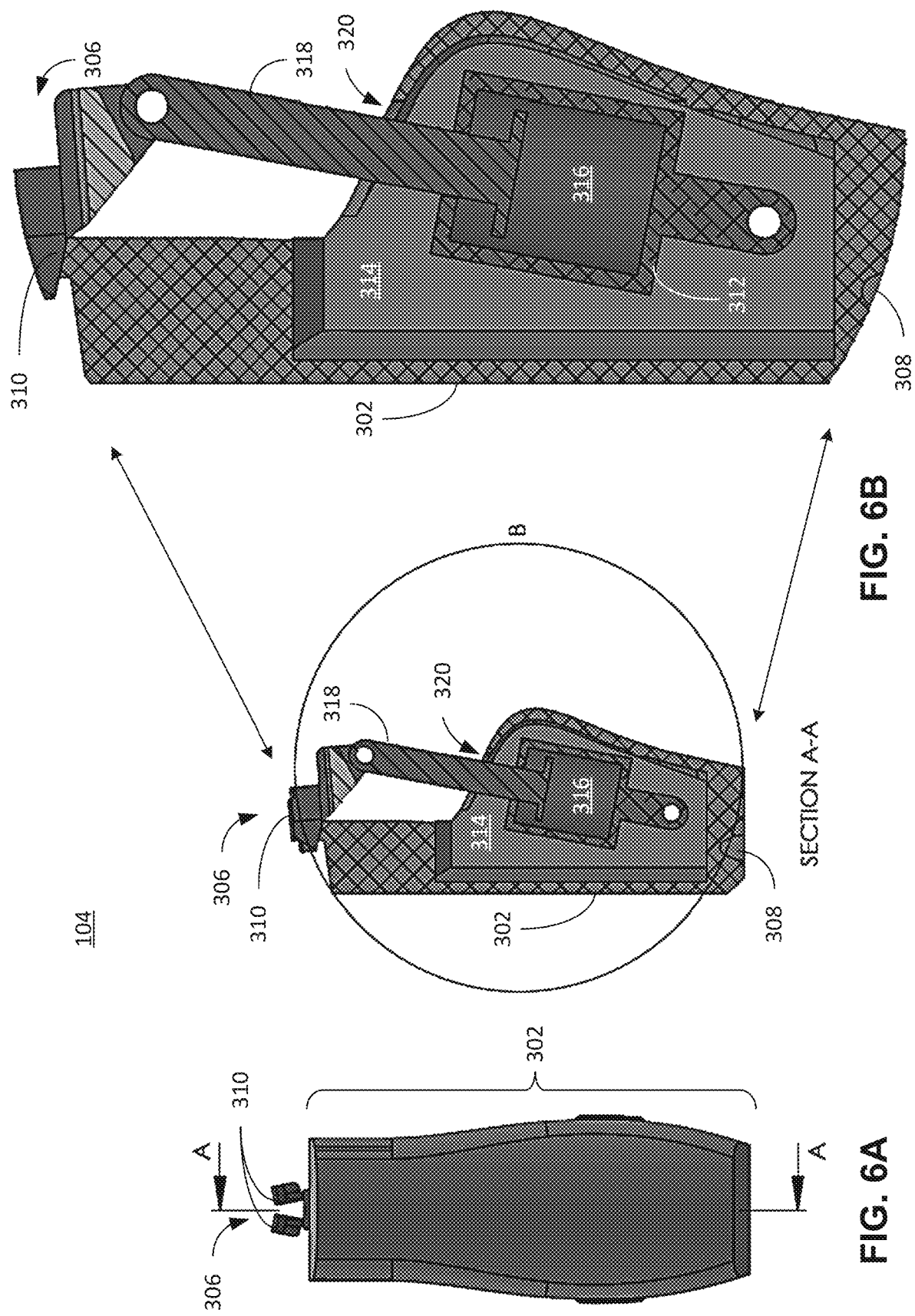

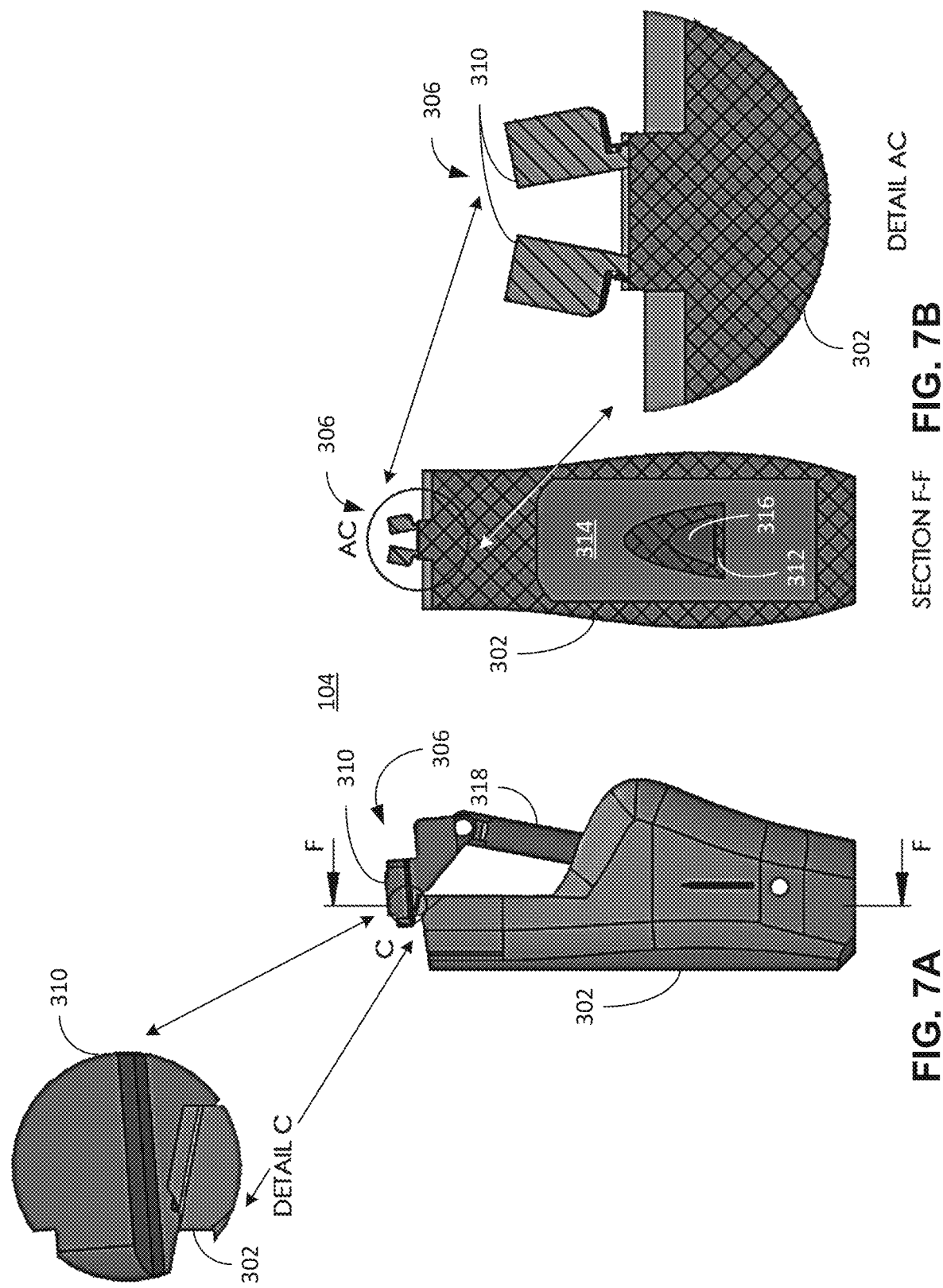

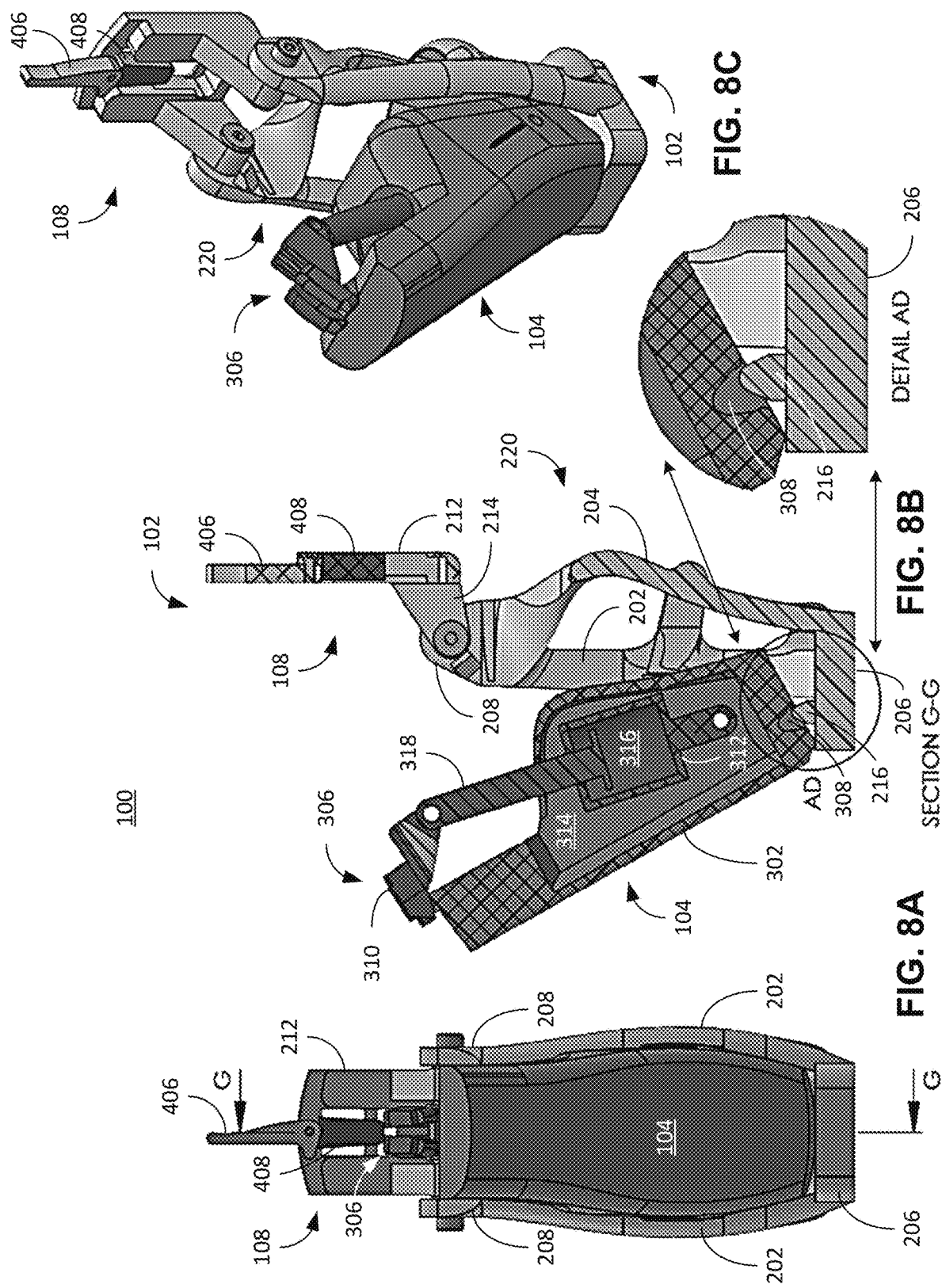

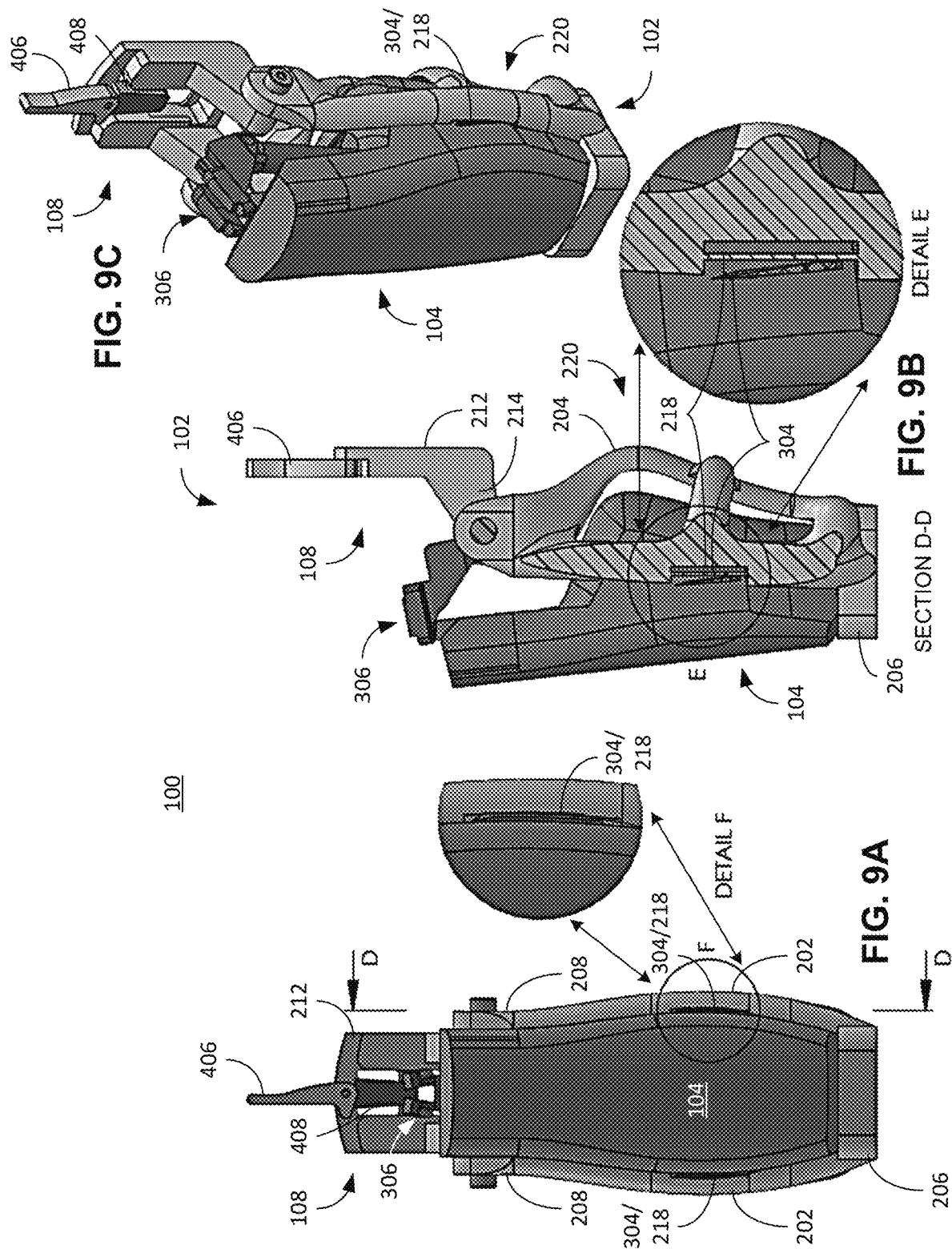

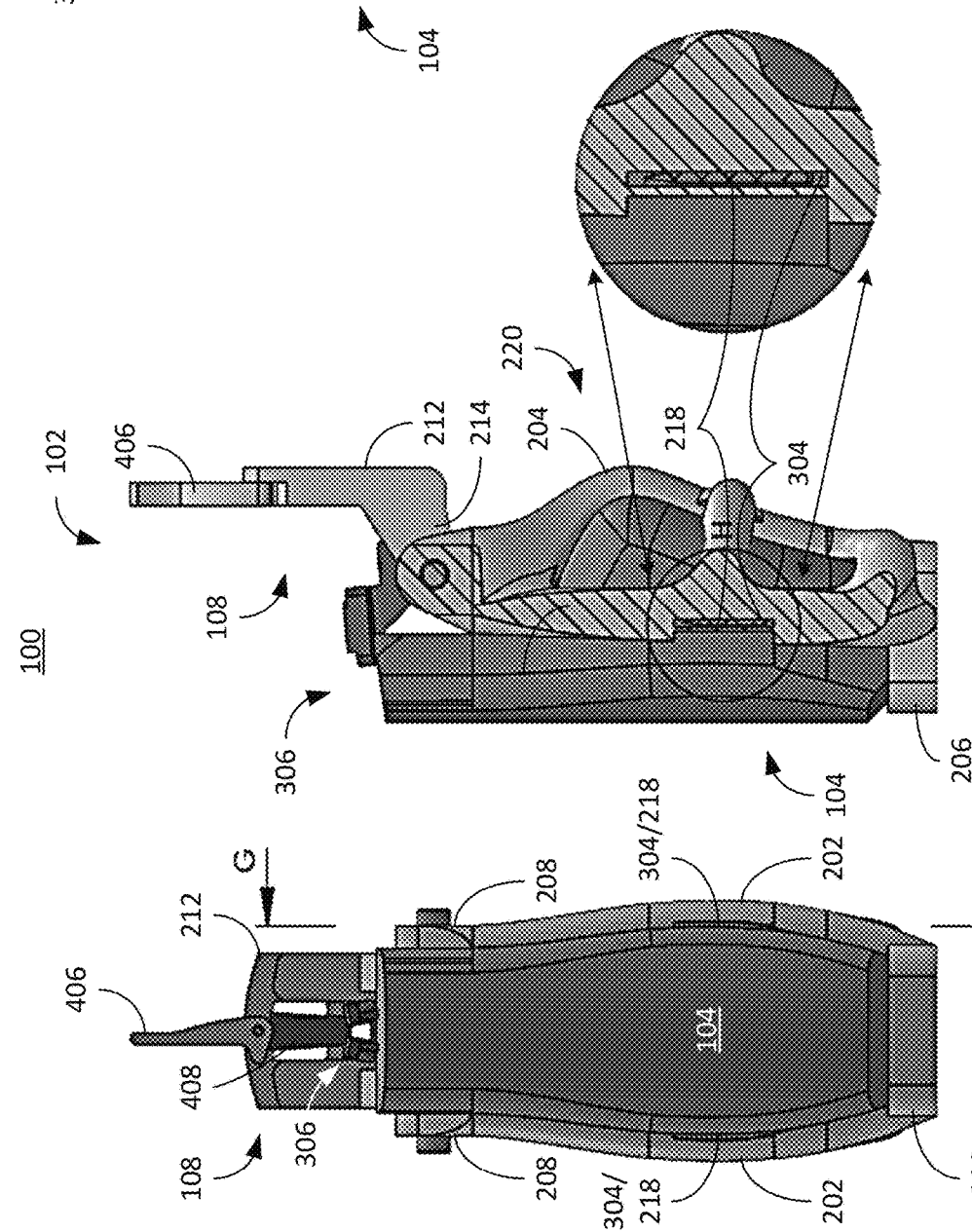

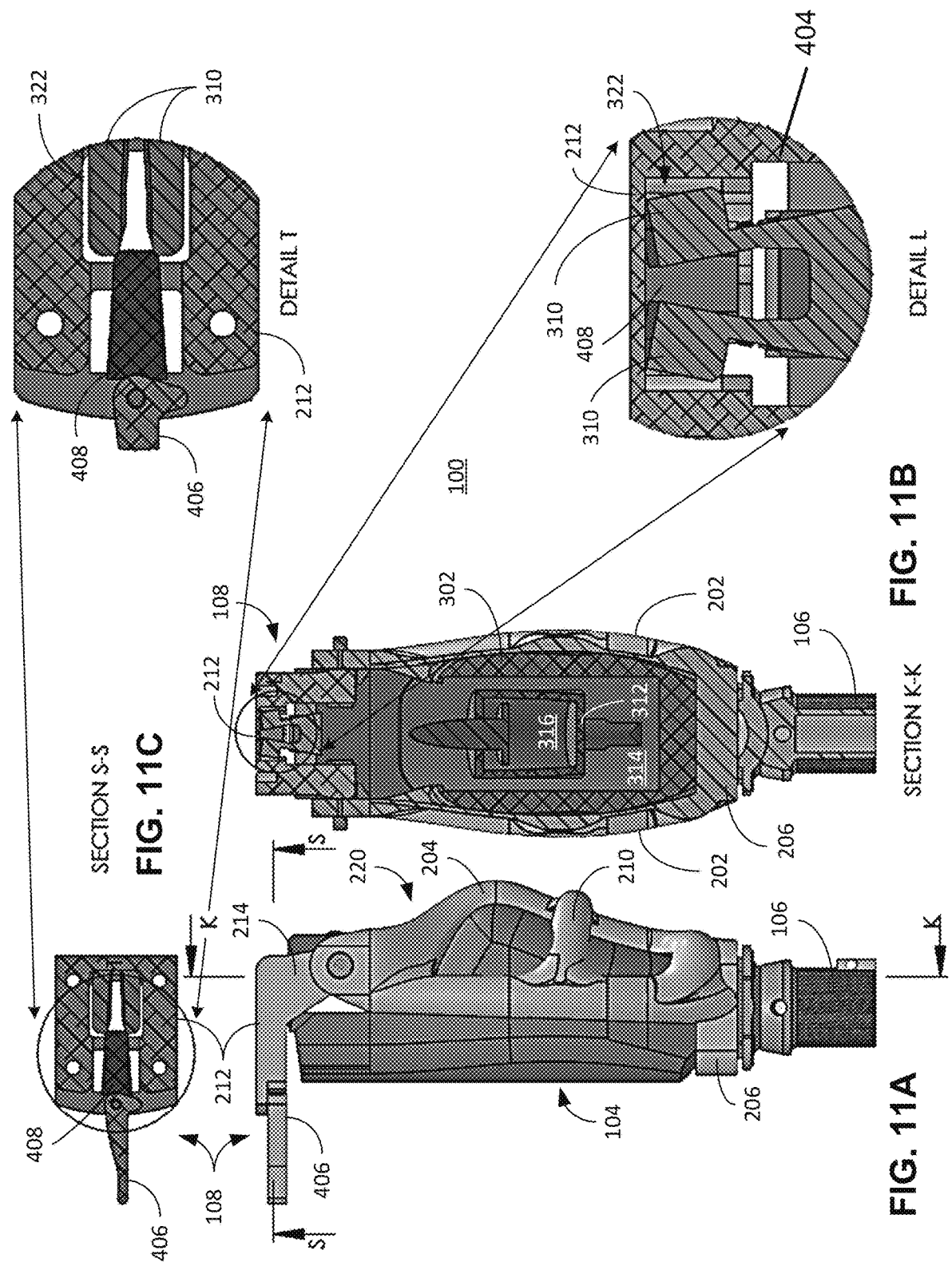

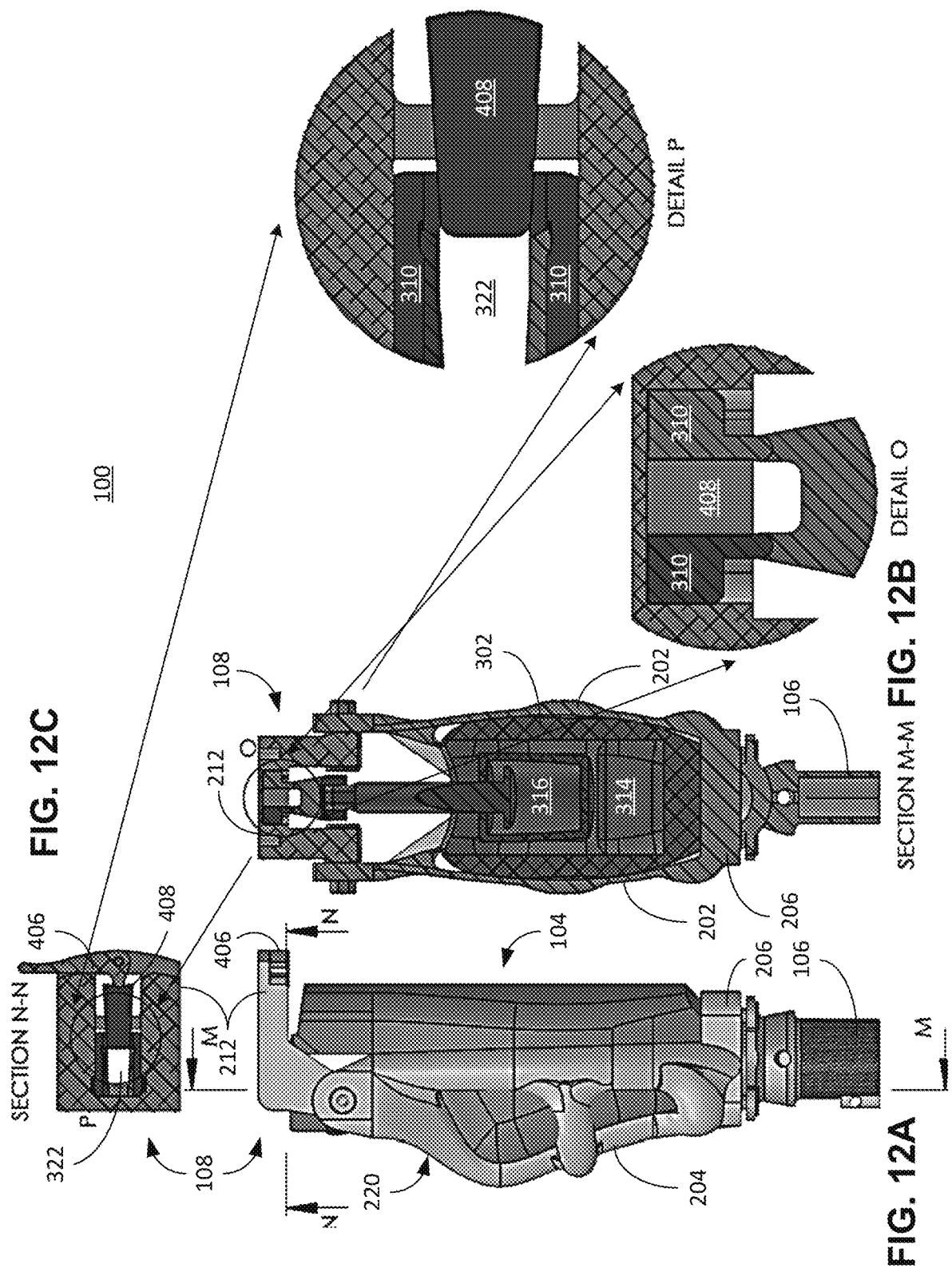

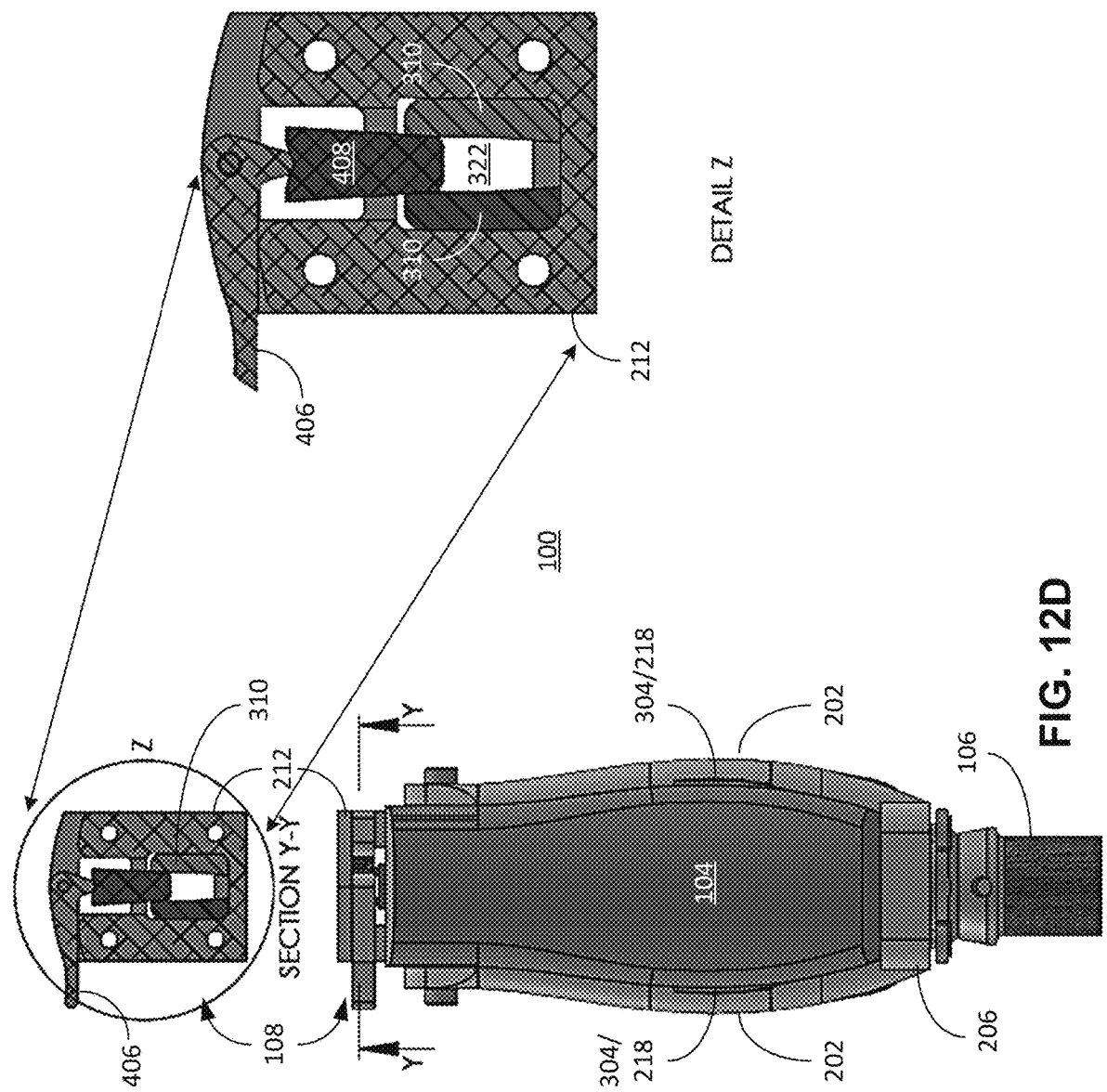

MODULAR PROSTHETICS DEVICES

CROSS-REFERENCE TO RELATED APPLICATIONS

The present application is a national stage entry pursuant to 35 U.S.C. § 371 of International Application No. PCT/US2018/049085, filed on Aug. 31, 2018, which claims the benefit of and priority to U.S. Provisional Application No. 62/553,586, filed on Sep. 1, 2017 and entitled "MODULAR PROSTHETICS DEVICES", both of which are hereby incorporated by reference herein in their entireties.

BACKGROUND

Prostheses can enhance the life of individuals who are missing one or more limbs by providing movement, support, and other functionality normally provided by the missing limbs. The design of the prostheses can vary depending on the functional needs and the desired appearance. For example, lower extremity prosthetics can take a wide range of implementations depending on the application. Significantly different implementations can be needed to support different physical activities. This can result in the individual owning multiple prostheses that are exchanged depending on the situation.

SUMMARY

Aspects of the present disclosure are related to modular prosthetics. In one aspect, among others, a modular prosthetic device comprises a chassis assembly comprising a joint portion; and an interchangeable module configured to be removably attached to the chassis assembly. In one or more aspects, the chassis assembly can be secured to a user by attaching the chassis assembly to an existing osseous implant or existing prosthetic socket. The chassis assembly can be secured at a proximal end to the joint portion and the mount portion can be secured to a distal end of the chassis assembly.

The chassis assembly can comprise the joint portion, a structural frame, and a mounting portion. The structural frame can accept the interchangeable module, where the interchangeable module can be secured to the chassis assembly via complementary mating slots and tabs on the structural frame and the interchangeable module. The interchangeable module can be secured to the joint portion via a locking mechanism, where the locking mechanism can be engaged with the joint portion via a lever and locking wedge. The locking mechanism can comprise a top snap configured to engage with the locking wedge to secure the joint portion to the interchangeable module. The top snap can be coupled to a damping mechanism of the interchangeable module. The damping mechanism can be a piston assembly. In various aspects, the chassis assembly can be configured to accept removable prosthetic modules attached to the mounting portion. The interchangeable module can comprise a damper driven mechanism. The modular prosthetic device can be selected from a leg, a lower leg, an arm, and a forearm. The joint portion can be securely attached to an existing osseous implant or existing prosthetic socket.

In one or more aspects, the joint portion can comprise a rotatable mounting plate configured to be secured to an implant or prosthetic socket of a user; and the interchangeable module can comprise a locking mechanism configured to engage an open cavity of the rotatable mounting plate to secure it in a load bearing position. The locking mechanism can comprise a pair of flanges configured to engage with a surface of the open cavity to secure the rotatable mounting plate in the load bearing position. The pair of flanges can tilt inward towards each other to facilitate insertion in the open cavity, and can flex outward to engage with the surface of the open cavity. The rotatable mounting plate can comprise a locking wedge that forces the pair of flanges to flex outward when inserted between the pair of flanges. The rotatable mounting plate can comprise a lever that forces the locking wedge between the pair of flanges when rotated from an extend position to a locked position. In various aspects, the chassis assembly can comprise an anchor on a module mounting surface at a distal end of the chassis assembly, and the interchangeable module can comprise a corresponding recess configured to align with the anchor when the interchangeable module is inserted into the chassis assembly. The interchangeable module and structural frame of the chassis assembly can comprise mounting ridges and mounting grooves configured to secure the interchangeable module in the structural frame.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure.

FIGS. 1A-1G provide computer generated views of an example of a modular prosthetic device, in accordance with various embodiments of the present disclosure. FIG. 1A is a top view, FIGS. 1B and 1D are side views, FIG. 1C is a front view, FIG. 1F is a rear view and FIGS. 1E and 1G are orthogonal views.

FIGS. 3A-3D provide computer generated views (top, front, side, and orthogonal, respectively) of an example of the chassis assembly of the modular prosthetic device of FIGS. 1A-1G, in accordance with various embodiments of the present disclosure.

FIGS. 5A-5D provide computer generated views of an example of an interchangeable module (top, front, side, and orthogonal, respectively) of the modular prosthetic device of FIGS. 1A-1G, in accordance with various embodiments of the present disclosure.

FIGS. 6A and 6B provide a computer generated view of an example of the interchangeable module of FIGS. 5A-5D, in accordance with various embodiments of the present disclosure. The A-A axis in FIG. 6A indicates the location of a cross-section through the module casing, exposing the interior of the module shown in FIG. 6B, where the damper driven portion of the interchangeable is located.

FIGS. 7A and 7B provide a computer generated example of another cross-section of the interchangeable module of FIGS. 5A-5D, in accordance with various embodiments of the present disclosure.

FIGS. 8A-8C, 9A-9C, 10A-10F, 11A-11C, and 12A-12D illustrate an example of the process of installing the interchangeable module into the chassis assembly of the modular prosthetic device of FIGS. 1A-1G, in accordance with various embodiments of the present disclosure.

DETAILED DESCRIPTION

Figure 1F:
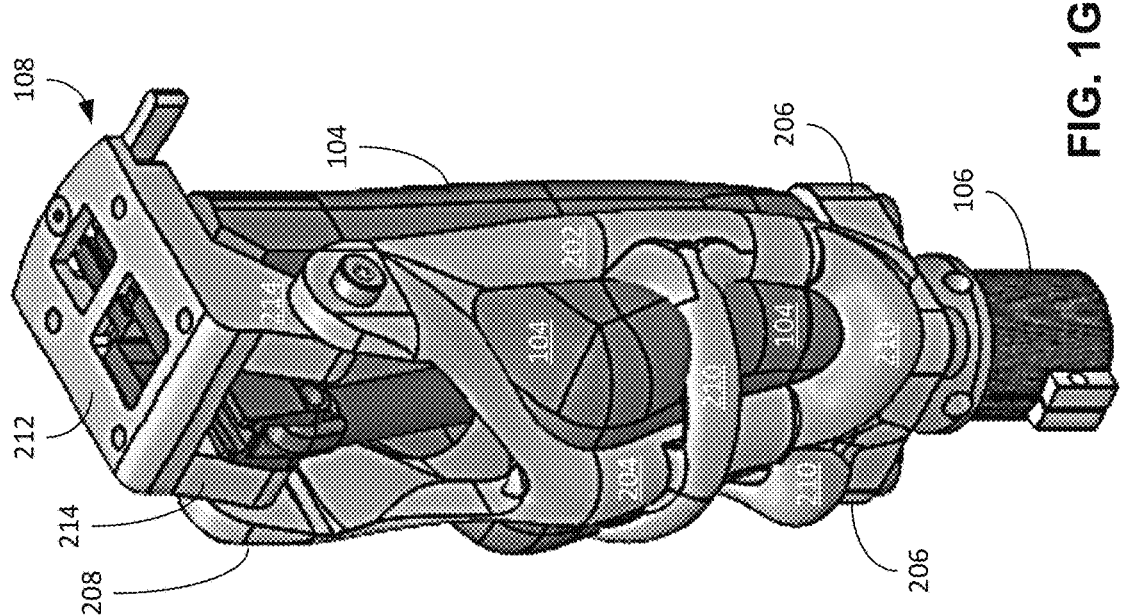

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of mechanical engineering, biomedical engineering, material science, and the like, which are within the skill of the art.

The following examples are put forth so as to provide those of ordinary skill in the art with a complete disclosure and description of how to perform the methods and use the devices disclosed and claimed herein. Efforts have been made to ensure accuracy with respect to numbers (e.g., amounts, temperature, etc.), but some errors and deviations should be accounted for.

Before the embodiments of the present disclosure are described in detail, it is to be understood that, unless otherwise indicated, the present disclosure is not limited to particular materials, configurations, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The present disclosure illustrates devices and systems for modular prosthetics. A prosthetic for amputees such as, e.g., above knee, below knee, above elbow, and/or below elbow, foot prosthetics can comprise an external chassis (or structural frame) in which prosthetist practitioners can set up a module or modular component allowing utilization of a specific application. The module or modular component can be inserted into the chassis and/or removed at will by the user thus allowing for multiple types of "modules" to be utilized for different applications in the same chassis. These modules can comprise a mechanical linkage reacting to forces implemented upon them by the engagement of the chassis. The chassis will accept modules that may be utilizing polymers, magnetics, micro-processing units and or shock absorbers. Modules can be inserted into the chassis in various ways of design either by snapping, clamping, magnetic or setting (resting) into the chassis itself from either the side, front, back or top insertion. The integration of many specific individual modules into a single chassis would allow a user(s) to have the freedom to switch out at any given point or time he or she may feel necessary to adapt to environmental changes, changes in terrain or changes in specific applied forces. This ability ito adjust gives a user(s) the option of multiple prosthetic choices or solutions in one prosthetic device. The chassis itself can be mounted to an existing or new prosthetic part either above or below allowing for the integration of various modules to be implemented & utilized.

Figure 1G:
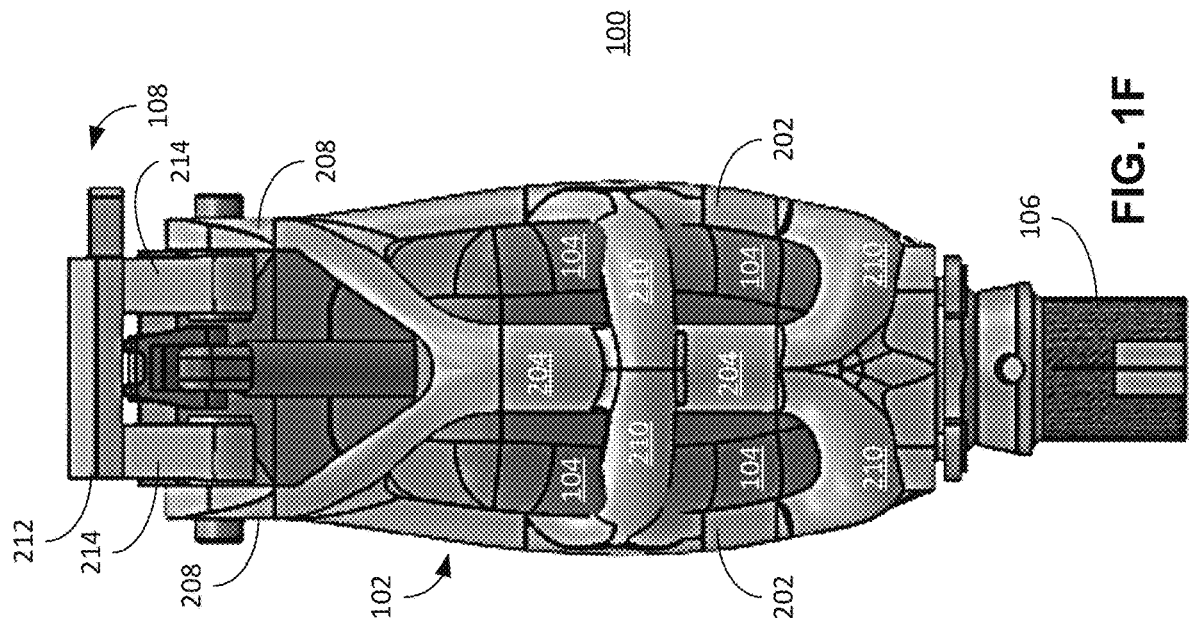

The present disclosure illustrates devices and systems for modular prosthetics that can be used for joints such as knees or elbows. Beginning with FIGS. 1A-1G, shown is an example of a modular prosthetic 100 that can be used as a knee joint. FIG. 1A is a top view, FIG. 1B is a right side view, FIG. 1C is a front view, FIG. 1D is a left side view, FIG. 1F is a rear view and FIGS. 1E and 1G provide perspective views of the prosthetic 100. The prosthetic 100 includes a chassis assembly 102 which can be coupled to a socket or other attachment device for use by a user. Interchangeable modules 104 for specific activities or environments can then be inserted into or attached to the chassis assembly 102. The prosthetic device allows for many levels of customization and can be easily changed by the user to suit his/her needs. Advantageously, the chassis assembly 102 is load bearing and can attach at the proximal end to an existing osseous implant or prosthetic socket of the user, eliminating the need for additional surgical procedures or costly new socket fittings. At the distal end, the chassis assembly 102 can include a mounting portion 106, which can be customized for the user's height. The mounting portion 106 can include a plate and screw adapter that can be modified to attach to a prosthetic attachment such as, but not limited to, artificial hands and feet. In the case of the lower leg example of FIGS. 1A-1E, the prosthetic attachment can include virtually any foot and/or pylon system available. An advantage to this configuration is that the user can incorporate existing foot and pylon configurations (e.g., running blades, skates, skis, cycling feet, etc.) already available on the market, eliminating the need for further customization and maximizing options.

Embodiments of the present disclosure include a custom chassis assembly 102 configured to accept interchangeable modules 104. In various embodiments, the prosthetic device 100 of the disclosure can be a limb or portion of a limb. In various embodiments, the interchangeable modules 104 can be designed to insert inside the chassis assembly 102, and can be secured using fastening mechanisms such as magnets, snaps, tabs, button clips, or other appropriate securing mechanisms.

In various embodiments, the interchangeable modules 104 can be configured to aid the user in adapting to the demands of specific activities, terrains, or environments. The interchangeable modules 104 can include damping devices, pistons, shock absorption mechanisms, or other types of suspension and control mechanisms. In some implementations, the interchangeable modules can include the ability to attach (e.g., snap, clamp, etc.) other compartments and/or components for specific applications (e.g., military or civilian such as a golf ball holder, etc.) to the module.

In various embodiments, the chassis assembly 102 can attach to the user at above-knee level. The chassis assembly 102 includes a joint portion 108 such as, e.g., a knee portion which can attach to the user's existing interosseous implant or prosthetic socket via an attachment mechanism such as, e.g., a plate. Other attachment mechanisms can be utilized for attaching the joint portion 108 directly to the user without a plate using, e.g., torque connectors, transcutaneous connectors, sliding locks, threaded pipes, button clips, and/or collar locks depending upon the type of ossteointegrated implant or socket in use. The joint portion 108 can be pivotally affixed to the structural frame of the chassis assembly 102 as illustrated in FIGS. 1A, 1B, 1C and 1E. The joint portion 108 can also include a mechanism (e.g., a lever and wedge, cam shaft, latch, pin, collar lock or other appropriate securing mechanism) for attaching and locking the interchangeable module into place. In some embodiments, the joint portion 108 is fastened to the structural frame of the chassis assembly using shoulder bolts and barrel nuts while not loading the threads of the fasteners in shear. In some embodiments, the chassis assembly 102 can be posteriorly convex in shape to mimic the shape of the calf. The module 104 can be shaped to conform to the shape of the chassis assembly 102. The module 104 can be retained within the open structural frame or can be molded to overlap a portion of the structural members of the chassis assembly 102. The exposed portion at the front of the module 104 can mimic the shape of the shin of the leg. In various embodiments, the chassis assembly 102 can be made from titanium, polymers, carbon fibers, aluminum, stainless steel, or combinations thereof.

FIGS. 1A-1G provide various views of an example of a modular prosthetic device 100 of the disclosure, demonstrating the chassis assembly 102 and the interchangeable module 104. In the example shown in FIGS. 1A-1G, the interchangeable module 104 is installed in the chassis assembly 102 and is shown engaged in the standing position. As can be seen, the structural frame of the chassis assembly 102 can be an open framework comprising a combination of structural members such as, e.g., horizontal and vertical structural members (or longitudinal and circumferential structural members). The combination of vertical and horizontal members can be arranged to transfer load forces between the mounting portion 106 and the joint portion 108, without exposing the module 104 to undue stress. The vertical and horizontal members can be shaped to approximate various body parts, while being able the handle the stresses imposed by use of prosthetic 100. For example, the structural frame can include two vertical side members 202 and a vertical central member 204 extending between a lower (or distal) mounting base 206 and upper (or proximal) attachment fixtures 208 for the joint portion 108. The vertical side and central members 202 and 204 can be curved or shaped to allow for insertion of an interchangeable module 104 into the framework.

In the side views of FIGS. 1B and 1D, the vertical side members 202 extend from the attachment fixtures 208 to the mounting base 206 on opposite sides of a longitudinal axis of the modular prosthetic 100. As shown in the front view of FIG. 1C, the vertical side members 202 curve outward as they extend between the proximal and distal ends. This can also be seen in the rear view of FIG. 1F. As illustrated in FIG. 1F, the central member 204 can extend from the mounting base 206 towards the joint portion 108. The central member 204 can include two arms that separate and extend to the attachment fixtures 208 to avoid interference with the joint portion 108. As shown in the side views of FIGS. 1B and 1D, the central member 204 can bend outward and then curve back inward as the two arms extend toward the attachment fixtures 208. One or more horizontal members 210 can extend between the vertical side members 202, and over the central member 204 to avoid distortion when pressure is applied to the prosthetic device 100. As can be seen in the example of FIGS. 1A-1G, the shapes of the vertical side members 202 and the central member 204 mimic the shape of the physical limb and allow sufficient space for the operating mechanisms of the interchangeable modules 104.

At the upper or proximal end, the chassis assembly 102 includes the joint portion 108, which is pivotally attached to the structural frame via the attachment fixtures 208 to allow for rotational motion of the mounting plate 212 (or other attachment mechanism) with respect to the structural frame. In the example of FIGS. 1A-1G, two pivot arms 214 extend from the mounting plate 212 and fit between the attachment fixtures 208. The location and orientation of the pivot arms 214 on the mounting plate 212 can be designed to allow for movement that mimics that of a natural joint, while allowing for operation of the installed module 104. The attachment fixtures 208 and pivot arms 214 include openings or holes that can be aligned to pivotally attach the joint portion to the structural frame. Fasteners such as, e.g., shoulder bolts and barrel nuts can extend through the openings to secure the joint portion 108 to the structural frame. In other implementations, the openings in either the attachment fixtures 208 or pivot arms 214 can be threaded to receive a bolt or screw passing through the opening in the pivot arm 214 or attachment fixture 208 to movably attach the joint portion 108 to the structural frame. The fasteners can be configured to prevent loosening of the connection between the attachment fixtures 208 and pivot arms 214 to avoid accidental disconnection during use of the prosthetic 100. One or more spacers or bushings can be positioned between the pivot arms 214 and attachment fixtures 208 (e.g., on the bolt, screw, or other fastener) to facilitate alignment and/or proper clearance. In addition, spacers (e.g., sleeves or bushings made from nylon, PTFE, or other appropriate material) can be included in the openings of the attachment fixture 208 and/or pivot arm 214 around the fastener to facilitate smooth movement of the pivot point.

In the example of FIGS. 1A-1G, the mounting plate 212 is shown with a substantially planar mounting surface for attachment to the socket or implant of the user, however other surface contours can also be provided. As shown in the top view of FIG. 1A, openings can pass through the mounting plate 212 to reduce weight while maintaining structural strength and integrity. The mounting plate 212 can include holes and/or openings to allow the joint portion 108 to be secured to the socket or implant of the user. In some implementations, an adapter can be affixed to the mounting plate 212 to allow the prosthetic 100 to be adjust for different socket or implant configurations. The mounting plate 212 is configured to attach to the module 104 opposite the implant mounting surface as will be discussed.

Figure 2:
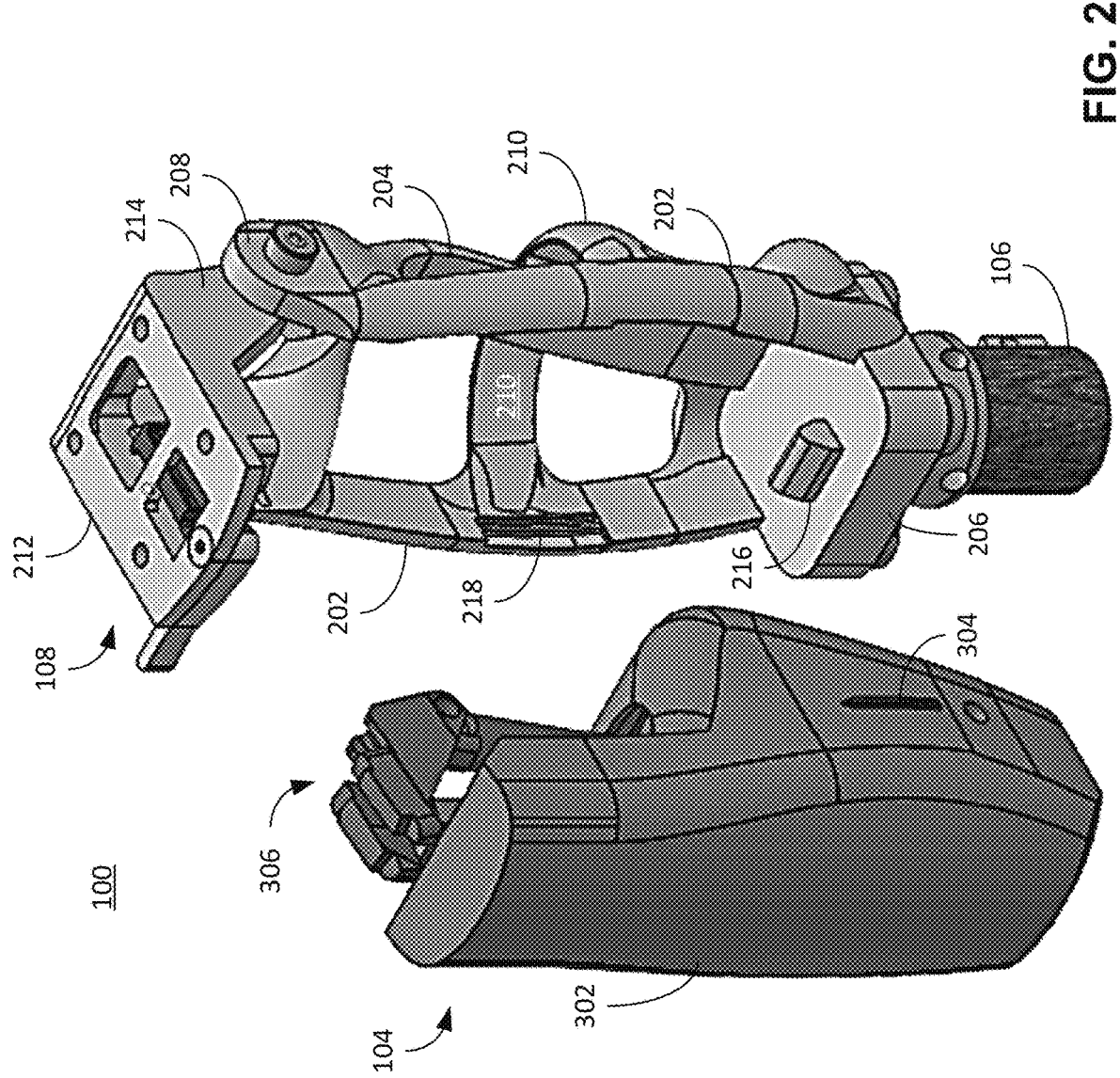
FIG. 2 provides a computer generated exploded view of an example of a chassis assembly and an interchangeable module of the modular prosthetic device of FIGS. 1A-1G, in accordance with various embodiments of the present disclosure.

At the lower or distal end, the chassis assembly 102 includes the mounting base 206, to which the mounting portion 106 can be attached. As will be discussed, the interchangeable module 104 can rest upon the mounting base 206 opposite the mounting portion 106 when installed in the chassis assembly 102. The mounting base 206 includes a base mounting surface configured to secure the mounting portion 106 to the mounting base 206. The mounting base 206 also includes a module surface opposite the base mounting surface that can receive one end of the interchangeable module 104. The module surface can be substantially planar as illustrated in FIG. 2, or can be shaped to match the contour of the end of the module 104. The chassis assembly 102 including the mounting base 206, structural frame with vertical and horizontal members, and attachment fixtures 208 can be fabricated as a single integral piece with the vertical side and central members 202 and 204 extending between the mounting base 206 and the attachment fixtures 208. In the example of FIGS. 1A-1G, a horizontal member 210 extends across an outer edge of the mounting base 206 between the two vertical side members 202. For example, the chassis assembly can be cast as a single unit and machined to the desired dimensions for use.

FIG. 2 shows an example of the modular prosthetic device 100 with the chassis assembly 102 and the interchangeable module 104 in a detached position. An example of the interchangeable module 104 is illustrated. As shown, the module 104 can include a module casing 302 shaped to conform to the inner shape of the chassis assembly 102. The inner surface of the structural frame can also be contoured (e.g., flattened or recessed) to match the outer surface of the module casing 302 as shown in FIG. 2. The chassis assembly 102 can include tabs and/or grooves that can align with corresponding features on the interchangeable modules 104 to secure the module 104 in place. For example, the mounting base 206 can include an anchor (or recess) 216 on the module surface which can be aligned with a corresponding recess (or anchor) on the bottom or end of the interchangeable module 104. The vertical side members 202 can also include mounting grooves and/or tabs 218 that can align with mounting ridges and/or depressions (or tabs and/or grooves) 304 on the sides of the module 104 to hold the module 104 in position. The mounting ridges and/or depressions 304 can snap into/onto the mounting grooves and/or tabs 218 of the structural frame for secure attachment of the module 104.

Referring to FIGS. 3A-3D, shown are various views of the chassis assembly 102 without an interchangeable module 104 installed. FIG. 3A shows a top view, FIG. 3B shows a front view, FIG. 3C shows a left side view, and FIG. 3D shows a perspective view of the chassis assembly 102. As can be seen in FIG. 3B, the grooves and/or tabs 218 align with one of the horizontal members 210. This can provide additional rigidity and strength for securing the interchangeable modules 104 in place. In addition, FIG. 3B illustrates the vertical central member 204 with two arms 222 that separate and extend to the attachment fixtures 208 to avoid interference with the joint portion 108. The shape of the arms 222 can be designed to handle the stress and strain placed on the structural frame during use.

Figure 4:
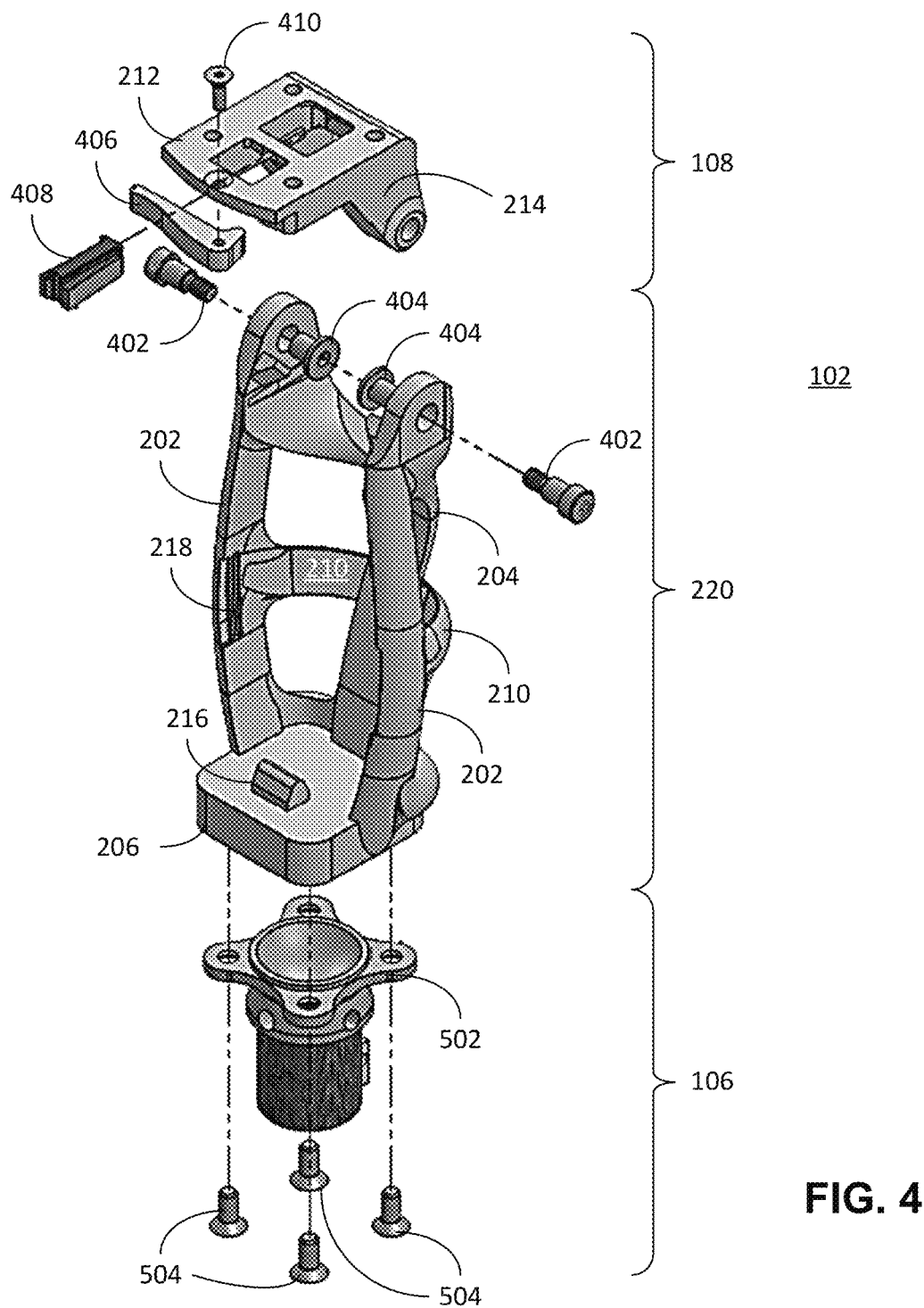
FIG. 4 provides a computer generated exploded view of an example of the chassis assembly of FIGS. 3A-3D, in accordance with various embodiments of the present disclosure.

Referring back to FIG. 2, an example of the interchangeable module 104 is illustrated. The module 104 includes a locking mechanism 306 that engages with the joint portion 108 to couple or engage the functionality of the module 104 with the chassis assembly 102. FIG. 4 shows an exploded view of the chassis assembly 102 including the joint portion 108, the structural frame 220, and the mounting portion 106. The joint portion 108 can include the mounting plate 212 (or other attachment mechanism) with two pivot arms 214 extending from one end of the mounting plate 212. The pivot arms 214 are sized to fit between the attachment fixtures 208, and both include openings or holes that can be aligned with corresponding opening or holes in the attachment fixtures 208 to allow the joint portion 108 to pivotally attach to the attachment fixtures 208 of the structural frame 220. Fasteners such as, e.g., shoulder bolts 402 and barrel nuts 404 can extend through the openings. Spacers and/or sleeves can be used to ensure proper alignment of the joint portion 108, and can be used to reduce friction. The joint portion 108 also includes a lever 406 and locking wedge 408, which facilitate coupling of the locking mechanism 306 of the interchangeable module 104 to the mounting plate 212. The lever 406 can be pivotally attached to the mounting plate 212 using, e.g., a recessed screw 410, bolt or other appropriate fastener. The lever 406 acts as a camshaft that linearly displaces the locking wedge 408 into the locking mechanism 306 by rotating the lever 406 about the screw 410, the tab at the proximal end moves the locking wedge 408 forward to engage with the top flap or flanges of the locking mechanism 306, thereby securing the module 104 to the joint portion 108.

The chassis assembly 102 includes the mounting portion 106, which can be detachably attached to the mounting base 206 of the structural frame 220 as illustrated in FIG. 4. The mounting portion 106 can include a mounting adapter 502 that can be secured to the mounting base 206 via one or more screws (e.g., 4 flat head hex drive stainless screws) or other appropriate fasteners 504. The mounting portion 106 may also be attached using other appropriate mounting methods such as, e.g., a sliding or rotating lock assembly. For example, a ball lock may be utilized. In various embodiments, the mounting portion 106 can be developed by a prosthetist to fit the user. At the distal end of the mounting portion 106, a lock and plate mechanism 506 can be fitted to provide a standardized fitting to attach virtually any foot and pylon systems (e.g., foot/ankle system, sprinting blades, cycling clip foot mounts, inflexible mounts, or elastic keel feet designed for particular activities) available to the user. Other attachment mechanisms can be fitted to accommodate various foot configurations, e.g., torque connectors, transcutaneous connectors, sliding locks, threaded pipes, button clips, and/or collar locks. Hand and/or other attachments may also be utilized for arm prosthetics.

Referring next to FIGS. 5A-5D, shown is an example of an interchangeable module 104. The interchangeable module 104 can take various forms (e.g., damper driven, robotic, computer controlled, etc.). For instance, shock/piston, EVA (e.g., rubber and/or polymer), microprocessor units (MPUs) or other components can be included in the interchangeable modules 104 to create a specialized unit or module to provide a specific result in applied applications.

In FIGS. 5A-5D, an example of a damper driven module 104 is illustrated. In various embodiments, the damper can be, e.g., hydraulic, pneumatic, electromagnetic, spring, etc. In various embodiments, the interchangeable module 104 can include a module casing 302, a locking mechanism 306, and a pivot point (or recess) 308 (FIG. 6B), which can be incorporated into the module casing 302. The locking mechanism 306 can include a top snap or flanges 310, which engage with the locking wedge 408 (FIG. 4) affixed to the mounting plate 212. The top snap can be configured to secure the interchangeable module 104 into the chassis assembly 102. As shown in FIG. 5A, the top snap of the locking mechanism 306 includes opposing flanges 310 that are angled inward toward each other. The flanges 310 are flexibly connected to the end of the module casing 302 opposite the pivot point 308. The connection allows the flanges 310 to flex outward, away from each other to engage with the mounting plate 212. In various embodiments, the interchangeable module 104 can be made from titanium, polymers, carbon fibers, aluminum, stainless steel, or combinations thereof.

FIGS. 6A and 6B illustrate a cross-sectional view of the damper driven module 104. The module casing 302 can enclose the interior mechanisms, such as the damper assembly 312 in an internal void 314. As shown in FIG. 6A, the cross-section (A-A) is taken along the centerline of the module 104 from the front side to the rear side between the two flanges 310 of the locking mechanism 306. The cross-sectional view A-A is presented in FIG. 6B. In the example of FIGS. 6A and 6B, the damper assembly 312 comprises a piston in a cylinder 316. Movement of the piston in the cylinder 316 is dampened by the fluid (e.g., oil, water, air or other suitable hydraulic or pneumatic fluid) in the cylinder 316. The amount of damping provided by the damper assembly 312 can be affected by the viscosity of the fluid, size of the cylinder 316, size of the piston, clearance between the piston and cylinder wall, or other appropriate design variable. The damping assembly 312 is connected to the locking mechanism 306 by a piston rod 318 that passes through an opening 320 in the module casing 302. The connection between the piston rod 318 and locking mechanism 306 is configured to rotate (e.g., about a connecting pin). As shown in the enlarged view of FIG. 6B, the top snap is connected to the module casing 302 at one end, while the other end is coupled to the piston rod 318 to a surface of the top snap opposite the flanges 310. For example, tabs can extend on both sides of the piston rod 318 with a connection pin extending through both the tabs and the piston rod. As the top snap moves about the connection point, the movement is transmitted to the piston, which moves within the cylinder 316. Such movement can dampen the effect of force applied to the mount plate 212 by the user. The opposite end of the cylinder 316 is also configured to rotate about a connection pin or shaft, which can extend across the module casing 302 through the internal void 314. This rotation can maintain alignment of the piston rod 318 in the damper assembly 312 as the top snap moves about the connection to the module casing 302.

FIGS. 7A and 7B illustrate another cross-sectional view of the damper driven module 104. As shown in FIG. 7A, the cross-section (F-F) is perpendicular to cross-section A-A of FIG. 6A and extends across the module 104 from the left side to the right side and passes through the flanges 310. The cross-sectional view F-F is presented in FIG. 7B, which shows the internal void 314 of the module casing 302 and a portion of the cylinder 316 of the damper assembly 312. Detail AC illustrates the relationship of the top snap or flanges 310 of the locking mechanism 306 and detail C shows the positioning of the top snap or flanges 310 on the module casing 302. As seen in detail AC, narrow sections are provided at the lower corners of the flanges 310 to allow for flexing and outward movement. Detail C shows a side view of the flexible connection with the module case 302. Magnetic ball, snap fit, or likewise can be used.

In various embodiments, the user can easily secure the interchangeable module 104 into the chassis assembly 102 without assistance. FIGS. 8A-13C illustrate an example of the process of installing the interchangeable module 104 into the chassis assembly 102. In FIGS. 1A-1G, the modular prosthetic 100 has been illustrated with the joint portion 108 in a standing position where the prosthetic would be load bearing with the mounting plate 212 substantially perpendicular to a longitudinal axis of the chassis assembly 102. To insert an interchangeable module 104, the user assumes a non-load bearing position (e.g., sitting), and loosens the lever 406 (e.g., rotating it outward) on the joint portion 108 of the chassis assembly 102, allowing the joint portion 108 to pivot into an open position as illustrated in FIGS. 8A-8C. In this position, the mounting plate 212 can be positioned substantially parallel with the longitudinal axis of the chassis assembly 102 as shown in FIGS. 8A-8C. FIG. 8A is a front view of the interchangeable module 104 being aligned with the anchor 216 of the chassis assembly 102. The lever 406 is shown rotated outward thereby allowing the locking wedge 408 to move to a retracted position. The cross-section G-G passing along the longitudinal axis, from front to rear, is shown In FIG. 8B. The interchangeable module 104 can be inserted at an angle into the chassis assembly 102 with the anchor 216 on the mounting base 206 aligned with the pivot point (or recess) 308 on the bottom of the module casing 302 as shown in FIG. 8B. This alignment between the anchor 216 and recess 308 is enlarged in detail AD. The corner of the module casing 302 can rest on the surface of the mounting base 206 as shown in FIG. 8C while positioning the pivot point 308 on the anchor 216.

The module 104 can then be rotated about the pivot point 308 and anchor 216 into the structural frame 220. As the interchangeable module 104 rotates about the anchor 216 and moves into the structural frame 220, the mounting ridges (or tabs) 304 on the sides of the module 104 contact the mounting grooves (or slots) 218 in the vertical side members 202 of the structural frame as illustrated in FIGS. 9A-9C. Detail F is an enlarged view illustrating the engagement of the mounting ridges (or tabs) 304 with the mounting grooves (or slots) 218. The cross-section D-D passing through one of the vertical side members 202 of the structural frame 220 is shown in FIG. 9B, where the mounting ridge (or tab) 304 is in contact with the vertical side member 202 prior to insertion into the mounting groove (or slot) 304. This is enlarged in detail E of FIG. 9B. Applying sufficient pressure to the front of the interchangeable module 104, the mounting ridges (or tabs) 304 can be inserted into the corresponding mounting grooves (or slots) 218. As can be appreciated, the vertical side members 202 of the structural frame can include mounting ridges (or tabs) and the module casing 302 can include mounting grooves (or slots) to provide the engagement.

Figure 10F:
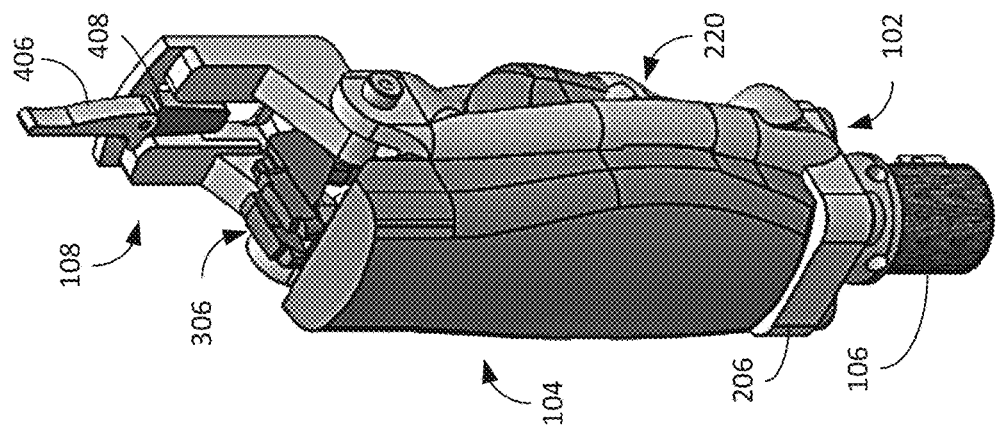
Figure 10E:
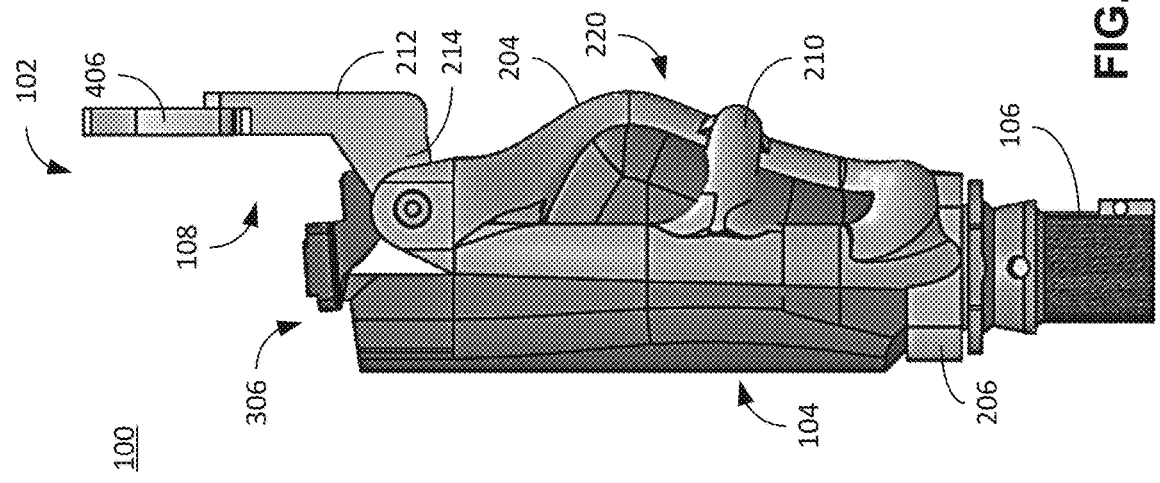
Figure 10D:
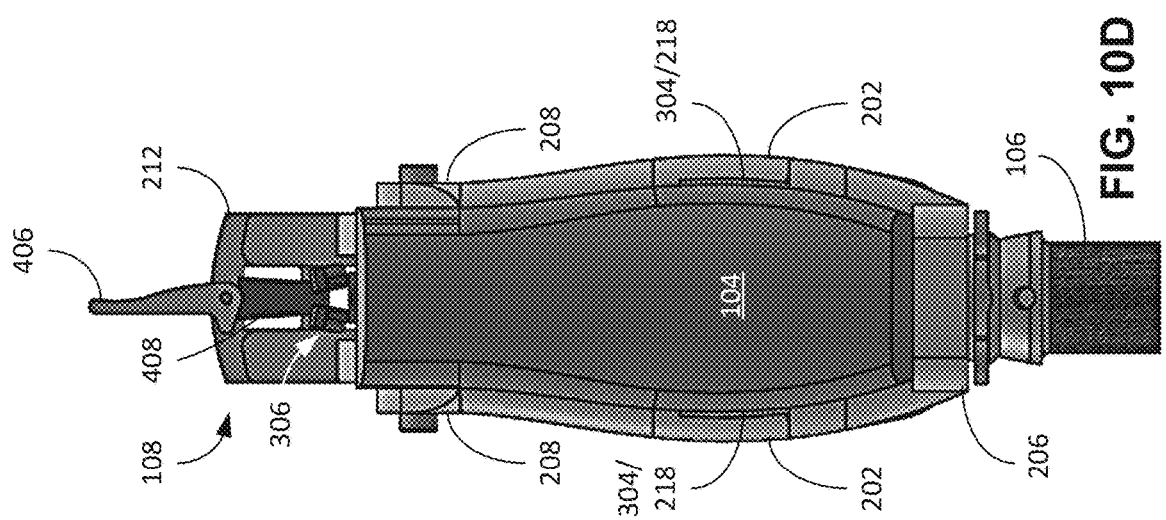

A snap fit can be achieved upon insertion of the interchangeable module 104 into the chassis assembly 102, providing an easy but secure assembly, as shown in FIGS. 10A-10C. The cross-section G-G of FIG. 10A passes through the same vertical side member 202 as in FIG. 9B. As is shown in FIG. 10B, the mounting ridge (or tab) 304 is snapped into the mounting groove (or slot) 304. This is enlarged in detail H of FIG. 10B. FIG. 10C shows the interchangeable module 104 secured in the structural frame 220 by the mounting ridges 304 in the mounting grooves 218. Application of force on the rear of the module 104, through the structural frame 220, can unsnap the interchangeable module 104 from the chassis assembly 102. FIGS. 10D, 10E and 10F show front, side and perspective views of the chassis assembly 102 with the interchangeable module 104 snapped in position and the mounting portion 106 attached to the mounting base 206.

With the interchangeable module 104 snapped into position, the user can stand up (or extend the leg) pivoting the joint portion 108 forward as illustrated in FIGS. 11A and 11B. In this position, the mounting plate 212 is in a load bearing position substantially perpendicular to the longitudinal axis of the chassis assembly 102. This motion will position the top snap of the locking mechanism 306 in line with the locking wedge 408 of the joint portion 108, as shown in the example in FIGS. 11A-11C. The cross-sectional view K-K of FIG. 11A is presented in FIG. 11B, which shows the internal void 314 of the module casing 302 and a portion of the cylinder 316 of the damper assembly 312. Detail L shows an enlarged horizontal view of the locking wedge 408 aligned with the top snap or flanges 310 of the locking mechanism 306. FIG. 11C shows the cross-section S-S of FIG. 11A, with detail T providing an enlarged vertical view of the locking wedge 408 aligned with the top snap or flanges 310 of the locking mechanism 306. As shown in details L and T, with the mounting plate 212 rotated into position, the top snap or flanges 310 are located within an open cavity 322 of the mounting plate 212. With the lever 406 extending outward as shown in FIGS. 11A and 11C, the distal end of the locking wedge 408 is adjacent to one end of the gap between the flanges 310. As can be seen in detail L, the inward tilt of the flanges 310 allow the top snap to easily align with the cavity 322 in the mounting plate 212. The pre-bent snap fit allows for a relatively minimal insertion and removal force.

Next, as shown in FIGS. 12A-12D, the lever 406 can be rotated flush with the front of the mounting plate 212. As the lever 406 is rotated about 90 degrees, the short tab presses against the end of the locking wedge 408. The lever action of this motion linearly displaces the locking wedge 408 into the top snap of the locking mechanism 306, spreading the flanges 310 of the top snap as the locking wedge 408 is forced between them. As the arms expand, they are forced apart enough to encompass the entire cavity 322 in the mounting plate 212. FIG. 12B shows the cross-sectional view M-M and FIG. 12C shows the cross-sectional view N-N indicated in FIG. 12A. As shown in details O and P, the top snap or flanges 310 are forced apart and engage with the outer surface of the cavity 322. With the locking wedge 408 inserted between the ends of the flanges 301, the flanges 301 can provide a friction fit with the sides of the open cavity 322 thereby locking the mounting plate 212 to the module 104. When the top snap or flanges 310 is fully installed and locked, the joint portion 108 locks in the XYZ coordinates, as shown in FIG. 12C. The cross-section Y-Y, and the enlarged detail Z, of FIG. 12D illustrates the positioning of the top snap or flanges 310 of the locking mechanism 306 with the lever 406 in the locked position with the locking wedge 408 secured between the flanges 310.

To uninstall the interchangeable module, the user will repeat the process in reverse. The lever 406 can be rotated outward allowing the locking wedge 408 to retract from between the flanges 310. The joint portion 108 can then be pivoted into an open position as illustrated in FIGS. 10A-10D, and the interchangeable module 104 removed from the structural frame 220 as previously discussed. Another module 104 can then be inserted and secured into position.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A modular prosthetic device, comprising:
    a chassis assembly comprising a joint portion, a structural frame, and a mounting portion; and
    an interchangeable module configured to be removably attached to the chassis assembly, wherein the structural frame accepts the interchangeable module, the interchangeable module secured to the chassis assembly via complementary mating slots and tabs on the structural frame and the interchangeable module, and the interchangeable module is further secured to the joint portion via a locking mechanism, wherein the locking mechanism is engaged with the joint portion via a lever and locking wedge.

2. The device of claim 1, wherein the locking mechanism comprises a top snap configured to engage with the locking wedge to secure the joint portion to the interchangeable module.

3. The device of claim 2, wherein the top snap is coupled to a damping mechanism of the interchangeable module.

4. The device of claim 3, wherein the damping mechanism is a piston assembly.

5. The device of claim 1, wherein:
    the joint portion comprises a rotatable mounting plate configured to be secured to an implant or prosthetic socket of a user; and
    the interchangeable module comprises a locking mechanism configured to engage an open cavity of the rotatable mounting plate to secure it in a load bearing position.

6. The device of claim 5, wherein the locking mechanism comprises a pair of flanges configured to engage with a surface of the open cavity to secure the rotatable mounting plate in the load bearing position.

7. The device of claim 5, wherein the chassis assembly comprises an anchor on a module mounting surface at a distal end of the chassis assembly, and the interchangeable module comprises a corresponding recess configured to align with the anchor when the interchangeable module is inserted into the chassis assembly.

8. A modular prosthetic device, comprising:
a chassis assembly comprising a joint portion and a structural frame, wherein the joint portion comprises a rotatable mounting plate configured to be secured to an implant or prosthetic socket of a user; and
an interchangeable module configured to be removably attached to the chassis assembly, wherein the interchangeable module comprises a locking mechanism configured to engage an open cavity of the rotatable mounting plate to secure it in a load bearing position, wherein the locking mechanism comprises a pair of flanges configured to engage with a surface of the open cavity to secure the rotatable mounting plate in the load bearing position, wherein the pair of flanges tilt inward towards each other to facilitate insertion in the open cavity, and flex outward to engage with the surface of the open cavity.

9. The device of claim 8, where the interchangeable module comprises a damper driven mechanism.

10. The device of claim 8, wherein the modular prosthetic device is selected from a leg, a lower leg, an arm, and a forearm.

11. The device of claim 8, wherein the joint portion is configured to be attached to an osseous implant or prosthetic socket.

12. The device of claim 8, wherein the rotatable mounting plate comprises a locking wedge that forces the pair of flanges to flex outward when inserted between the pair of flanges.

13. The device of claim 12, wherein the rotatable mounting plate comprises a lever that forces the locking wedge between the pair of flanges when rotated from an extend position to a locked position.

14. A modular prosthetic device, comprising:
a chassis assembly comprising a joint portion and a structural frame; and
an interchangeable module configured to be removably attached to the chassis assembly, wherein the interchangeable module and structural frame of the chassis assembly comprise mounting ridges and mounting grooves configured to secure the interchangeable module in the structural frame.

15. The device of claim 14, wherein the chassis assembly is configured to be secured to an osseous implant or prosthetic socket.

16. The device of claim 14, wherein the chassis assembly comprises the joint portion, the structural frame, and a mounting portion.

17. The device of claim 16, wherein the joint portion is secured at a proximal end of the chassis assembly and the mounting portion is secured to a distal end of the chassis assembly.

18. The device of claim 16, wherein the structural frame accepts the interchangeable module, the interchangeable module secured to the chassis assembly via complementary mating slots and tabs on the structural frame and the interchangeable module.

19. The device of claim 16, wherein a prosthetic attachment is attached to the mounting portion.

20. The device of claim 14, where the interchangeable module comprises a damper driven mechanism.

* * * * *